(12) United States Patent
Mikus (10) Patent No.: US 10,471,281 B2
(45) Date of Patent: Nov. 12, 2019

(54) METHOD FOR DIRECT BONE STIMULATION DURING INTERVENTIONAL PROCEDURE TO ASSIST IN BONE HEALING

(71) Applicant: MISONIX, INCORPORATED, Farmingdale, NY (US)

(72) Inventor: Paul Mikus, Coto de Caza, CA (US)

(73) Assignee: MISONIX, INC., Farmingdale, NY (US)

(*) Notice: Subject to any disclaimer, the term of this patent is extended or adjusted under 35 U.S.C. 154(b) by 827 days.

(21) Appl. No.: 14/938,280

(22) Filed: Nov. 11, 2015

(65) Prior Publication Data

US 2016/0129284 A1   May 12, 2016

Related U.S. Application Data

(60) Provisional application No. 62/078,700, filed on Nov. 12, 2014.

(51) Int. Cl.

| A61N 7/00 | (2006.01) |
|---|---|
| A61N 2/00 | (2006.01) |
| A61N 2/02 | (2006.01) |
| A61N 1/20 | (2006.01) |
| A61N 1/32 | (2006.01) |

(52) U.S. Cl.
CPC ............... *A61N 7/00* (2013.01); *A61N 1/205* (2013.01); *A61N 1/326* (2013.01); *A61N 2/002* (2013.01); *A61N 2/02* (2013.01); *A61N 2007/0013* (2013.01)

(58) Field of Classification Search
CPC .......... A61N 2/00; A61N 2/002; A61N 2/004; A61N 2/02; A61N 7/00; A61N 2007/0013; A61N 1/326; A61B 17/14
See application file for complete search history.

(56) References Cited

U.S. PATENT DOCUMENTS

| 4,768,504 A * | 9/1988 | Ender | A61B 17/142 30/166.3 |
|---|---|---|---|
| 6,678,562 B1 * | 1/2004 | Tepper | A61B 17/6416 606/54 |
| 6,701,185 B2 * | 3/2004 | Burnett | A61N 1/36071 607/149 |
| 2009/0131838 A1 * | 5/2009 | Fotiadis | A61B 5/0031 601/2 |

* cited by examiner

*Primary Examiner* — Carrie R Dorna
(74) *Attorney, Agent, or Firm* — R. Neil Sudol; Henry D. Coleman (57) ABSTRACT

A surgical method uses a surgical instrument having an operative tip or end effector and an applicator of energy having an energy-transmitting interface, the applicator being different from the surgical instrument and separate therefrom. The method contemplates conducting an interventional procedure including steps of: (i) manipulating the instrument to place the operative or end effector in contact with bone tissue of a patient at a surgical site, (ii) using the surgical instrument to surgically operate on the bone tissue at the surgical site, (iii) prior to a termination of the procedure, manipulating the applicator to place the interface in contact with bone of the patient at or proximate the surgical site, and (iv) operating the applicator to apply, to the bone via the interface, energy with parameters of type, intensity, and duration selected for stimulating the healing of bone tissue.

12 Claims, 3 Drawing Sheets

METHOD FOR DIRECT BONE STIMULATION DURING INTERVENTIONAL PROCEDURE TO ASSIST IN BONE HEALING

BACKGROUND OF THE INVENTION

The present invention relates to a method for promoting the healing of bone tissue which is subjected to surgery or other interventional procedures. The invention also relates to associated apparatus for use in the method.

Boyer described the use of electrical energy to heal tibial fractures in 1816 (Boyer, 1816). Wolff published in 1892 what is know today as Wolff's Law, stating the structure of bone adapts to changes in its stressed environment (Behrens, 2013). Thus the application of energy to bone creates the potential for artificial stresses that can result in the bone responding. The response is the stimulatory result of the application of artificial stresses.

The application of artificial stresses to bone by energy is bounded or delimited by other potential tissue effects. The most prevalent of these is the production of heat. Continuous application of energy to bone can result in thermal damage to either the application site or the treatment site. Thus upper limit of application of energy that can result in therapeutic bone stimulation is the point at which the application of that energy causes thermal damage.

This upper limit was a prohibiting factor in the use of ultrasound as an energy source for application to bone in general. A variety of treatment modalities for therapeutic application of ultrasound were explored with success from the 1930's forward, but bone treatment was viewed as a limitation due to the potential to damage the bone rather than stimulate it.

In 1950, Maintz published the first study describing the positive stimulatory effect of ultrasound on bone (Schortinghuis, 2003). The study in rabbits did not confirm an accelerated bone healing effect by ultrasound, but noted that periosteal new bone formation could be produced. The first human study reporting the treatment of slow or non-uniting fractures by ultrasound was published in 1953 (H Hippe, 1953).

A renewed interest in the use of ultrasound for bone stimulation and healing began with research using low dose pulsed ultrasound to overcome the issue of thermal damage (Shiro, 1964). This type of application of energy employed pulsed ultrasound at an intensity of 0.2 $W/cm^2$. The low energy density application stays below a threshold of thermal build up avoiding the potential for thermal damage. The challenge with lower dose energy applications is to be above the lower limit threshold of clinical effect. So the application of energy must be of sufficient density and duration to cause an effect to occur without causing thermal damage at the treatment site.

Low intensity pulsed ultrasound allows for application of the energy from a distant site, resulting in a non-invasive treatment. The application of the energy is easily transmitted from a non-invasive site to the internal targeted bone that requires stimulation or healing. Ultrasound waves transmit well through tissue, making a potential treatment application one that starts at the skin and continues to the treatment site and beyond. This non-invasive approach requires energy levels at the skin to be higher to compensate for the required energy densities that will be between the lower limit of tissue (bone) response and the upper limit of thermal damage.

Electrical energy can be transmitted from the skin to the targeted area. The challenge in utilizing electrical energy for non-invasive applications is the potential for both muscle and nerve tissue in the transmitting path to cause either contractions or pain. The type of tissue in the transmission path and the potential for unwanted tissue response not at the targeted area represents another limitation to the application of energy for bone stimulation or healing.

One method to overcome several of these limitations is the implantation of devices that remain resident in the body. The implantation results in a closer proximity to the treatment site, reducing the risk for unwanted tissue response in the transmission path. Additionally in the implantation approach the risk is reduced for thermal damage at the skin, in the transmission path, or at the targeted treatment zone because lower energy densities are required due to the closer proximity of the energy source to the targeted treatment zone. For example, implantable devices can include DC stimulation devices or pulsed electromagnetic fields (PEMF) which implant the applicators at the fusion site and the power source is either implanted or delivered by inductive coupling (Gan, 2006). The limitation of this approach is the need to implant a device in the patient for a significant period of time postoperatively in order to achieve the treatment effect.

The challenge in either a non-invasive only or implantable device only is to remain with the lower and upper limits of energy density to enable effective bone stimulation and healing. Both approaches mitigate the problem of energy density deposition remaining within the upper and lower threshold limits by applying energy over a long duration and frequency. For example, low intensity pulsed ultrasound (LIPUS) treatment protocols may range, with 20 minute daily application, from 2 weeks to 40 days (Erdogan, 2009). The limitation of long duration or frequency of treatment application is the reliance on the patient for compliance in consistent application.

A variety of methods have been described to stimulate bone in order to encourage healing. For example, U.S. Pat. No. 4,530,360 Duarte describes a method of applying pulses of ultrasound non-invasively daily over a period of weeks to months. The power density is noted to be below thermal damage thresholds of the application and target treatment sites. The limitation in this approach is the need to apply sufficient amounts of power density to transmit from the skin to the bone treatment site, while staying below the thermal damage threshold. The resulting treatment parameters require a long duration of application measured in weeks to months.

U.S. Pat. No. 5,191,880 describes a method to mechanically stimulate bone growth or healing. The application of either mechanical, electrical or ultrasound energy at high frequencies (between 10 to 50 hertz) mimics the resonant frequency that naturally occurs in movements such as walking, to produce mechanical loads on the bone. These mechanical loads are meant to stress the bone in order to promote a growth or healing response. The limitation to this approach is that the stress imparted to the bone is inherently damaging. The underlying condition for lack of bone density (osteopenia for example) would limit the response to the applied mechanical stresses. This method does not attempt to stimulate bone cells directly to initiate bone cellular activation and upregulation of genes and growth factors.

U.S. Pat. No. 5,441,527 describes a method for an implantable bone stimulation device that delivers alternating current. The energy is delivered over a period of time and the implant is left in place during the entire treatment regimen.

The inherent limitation of this device is the need to leave behind an implantable device in order to derive the benefit of delivering therapeutic bone stimulation at or near the target.

U.S. Pat. No. 5,496,256 describes an implant with disposable ultrasound transducers for healing in dental applications. The implant involves the application of ultrasound energy to accelerate healing of bone grafts in the jaw. The limitation of this approach is the use of an ultrasonic implant held in place by an implantable screw in order to aid healing of either another implant or a bone graft.

U.S. Pat. No. 5,547,459 describes a non-invasive ultrasound bone stimulation device that utilizes a set of ultrasonic signals to determine the optimal dose of exogenous application. The resulting dose is delivered with a spatial-average time-average (SATA) power density of around 45 mW/cm$^2$. The limitation of this device is the need to deliver a higher power density at the exogenous application site in order to achieve the optimal dose at the bone treatment site.

While a number of non-invasive or implantable bone stimulation devices have been previously disclosed, what does not exist and what would be beneficial to the market is a method to apply bone stimulation directly during interventional procedures, and or in combination with postoperative and/or pre operative bone stimulation applications to assist bone healing post intervention.

SUMMARY OF THE INVENTION

The present invention aims to improve the healing of bone tissue that is subjected to interventional surgical procedures such as ablation and dissection. In brief, the invention contemplates direct bone stimulation during interventional procedures to cause better healing rates post bone intervention.

The application of bone stimulation during an interventional procedure overcomes the limitations of compromised energy density from non-invasive application or the need to implant a device that delivers energy directly to the treatment area of a bone.

Direct bone stimulation is implemented by placing an applicator on or near the bone area that is under repair during the interventional procedure. The placement of the applicator preferably includes attaching the applicator to the bone, the applicator being effective to conduct a predetermined amount of energy into the bone for a preselected period of time during the interventional procedure to stimulate healing processes in the bone. The applicator incorporates or is operatively linked to an energy source programmed or configured for generating energy of a predetermined intensity for the preselected period of time. The energy may be applied in pulses or at intervals within the prescribed period. The application of the bone stimulating energy kick-starts a bone growth process at the exact time when the bone injury is occurring, thus yielding a highest possible impact for tissue recovery. The bone injury that occurs during an interventional procedure can be mitigated by the application of bone stimulation such that the bone response is amplified.

The interventional procedure can be an open surgical procedure or a minimally invasive procedure to correct a clinical problem involving a bone structure in the body. In the case of a minimally invasive procedure, the energy applicator may be disposed at the distal end of a thin rod or shaft (or more than one in the case of bipolar electrical stimulation) that is inserted through the patient's overlying tissues. The applicator rod or shaft may be held in place during the interventional procedure by a mounting frame external to the patient.

The stimulation of natural bone repair processes can be achieved by a variety of energy sources. For example, electrical stimulation, DC and/or AC, can be applied by the applicator to the surgical site during the procedure in order to stimulate bone healing and growth processes. In using DC current, one typically applies anode and cathode to the bone on opposite sides of the treatment site, the current being of sufficient strength to cause bone stimulation at the bone treatment site. Similarly, in the application of AC current electrical contacts can be placed to engage the bone on opposite sides of the surgical or treatment site, the generation of alternating electric fields overlapping the bone treatment site in sufficient strength to stimulate bone healing, tissue repair and cellular growth. It is also possible to use a monopolar configuration, with one electrode placed in direct contact with the bone at or proximate the surgical/treatment site and another electrode placed on a skin surface of the patient proximate the surgical site, preferably on a side thereof partially opposed to the position of the bone-engaging electrode.

The stimulation of natural bone repair processes can be achieved by the application of magnetic field energy. In that case, one or more electromagnets can be positioned as close as possible to the surgical or treatment site, the electromagnets having sufficient windings and core magnetic permeability and carrying sufficient current to generate magnetic field lines of effective intensity in or near the surgical/treatment area.

In a preferred embodiment, ultrasound energy is delivered by an applicator at or near the bone treatment site during an interventional procedure with the energy being of an intensity and duration effective to induce the onset of bone healing processes. For example an ultrasound transducer can be positioned in contact with a bone at or near a treatment area during an interventional procedure to optimize energy density delivery directly to the treatment area for stimulating the healing of bone tissues damaged or impacted as a result of the intervention. The application of the bone stimulating ultrasound energy occurs immediately, right at the time of injury inflicted during the interventional procedure in an attempt to correct a clinical problem. Thus the benefit of the application of the bone stimulation intraoperatively—contemporaneously with the interventional procedure and as a part of the interventional procedure—is both the direct application at the site and the fastest time to treatment from the occurrence of the bone injury.

Ultrasound energy is delivered to the bone tissue so that one or more of a number of bone growth stimulation effects occur. For example, ultrasound can be applied in sufficient strength to cause mechanical vibration of the bone at resonant frequencies that mimic naturally occurring stresses to the bone. Those mechanical stresses as a result of resonant frequencies prompt a response by the bone tissue that begins or accelerates a healing process. The resonant frequencies may be determined in a calibration process commenced upon placement of an ultrasound transducer on the bone. In that case the energy applicator, or a calibration instrument placed in contact with the bone, measures bone vibration and determines a resonance or near-resonance ultrasonic frequency. Alternatively, a resonance frequency can be determined via computer calculation from the geometry of the target bone, the contemplated surgical/treatment site, and the velocity of ultrasonic wave conduction through the bone tissue.

Another example of the type of bone stimulation via ultrasound application is stimulation that occurs at a cellular level, leading to acceleration of bone growth factors that contribute to the healing process. The ultrasound energy is directly applied to the bone treatment site with an energy density of sufficient strength to induce a bone stimulation process coincident with the time of injury (interventional treatment) and at the most optimal time to begin the healing process.

The ultrasound applied in an intraoperative healing process pursuant to the present invention is generated in low frequency ranges, those below 100 Khz. While a wide variety of energy densities can be used, energy densities in the 25 mW/cm$^2$-45 mW/cm$^2$ range are preferred. These energy densities appear to deliver the most optimal energy density while maintaining no or limited thermal response in the bone.

Since application of healing-stimulating energy pursuant to the present invention is directly to bone tissue, transmission through soft tissues overlying the treatment site is avoided, so that higher energy densities can be delivered while staying below thermal damage thresholds and upper limits. Thus a wide range of bone stimulation parameters can be used for direct interventional ultrasound application for advancing natural cellular healing and tissue repair processes.

The duration of energy application may include a wide variety of protocols. For example, interventional direct application of bone stimulating ultrasound can be applied for the length of a surgical procedure and initiated once the surgeon has gained access to the treatment area. Conventional bone stimulation treatment protocols require application in durations measured in weeks and months. One of the benefits of the invention is a shortened application time by virtue of the direct access and proximity in time to the injury of the bone treatment site. While a wide variety of treatment duration protocols can be followed, a preferred approach is direct application of bone stimulating energy for a minimum of 20 minutes during the surgical intervention and a maximum of the entire length of the surgical procedure, which may last several hours or more.

The application of the therapeutic energy may be continuous or intermittent. For instance, the energy may be applied in pulses each ranging in duration from a few microseconds to several minutes. The interpulse durations may likewise vary in duration from a few microseconds to several minutes.

Additionally the bone healing treatment energy can be augmented by a pretreatment conditioning of the bone site non-invasively to work in conjunction with the direct interventional application of bone stimulation. A composite pretreatment and intraoperative treatment protocol serves to amplify the bone stimulation effect. Pretreatment energy is typically implemented via a dedicated applicator, optionally paired with an intraoperative applicator as part of a bone stimulation kit. A common energy source or generator can be used to drive both pretreatment and intraoperative applicators, where the two types of treatment involve the same type of energy.

Similarly, a postoperative applicator can be combined with the intraoperative applicator to extend of magnify the bone stimulation effect. The postoperative applicator can be utilized to continue the bone stimulation process begun in the intraoperative application. An applicator for a post treatment application can be packaged with an intraoperative applicator in a bone stimulation kit. A common energy source or generator can be used to drive both pre treatment and intraoperative applicators.

Preoperative bone stimulation, intraoperative bone stimulation and postoperative bone stimulation can all be carried out to maximize bone healing effects. A treatment protocol begins by a pretreatment conditioning of the bone site non-invasively. The pretreatment works in conjunction with a direct application of bone stimulation energy intraoperatively. Use of a postoperative applicator can follow the intraoperative procedure and extend the bone stimulation effect. A bone stimulation kit for implementing the tripartite procedure includes a pretreatment applicator, an intraoperative applicator and a post treatment applicator. A single energy source can be used to drive all three applicators in seriatim.

A surgical method comprises (a) providing a surgical instrument having an operative tip or end effector, (b) providing an applicator of energy, the applicator being different from the surgical instrument and separate therefrom, the applicator having an energy-transmitting interface, and (c) conducting an interventional procedure including steps of: (i) manipulating the instrument to place the operative or end effector in contact with bone tissue of a patient at a surgical site, (ii) using the surgical instrument to surgically operate on the bone tissue at the surgical site, (iii) prior to a termination of the procedure, manipulating the applicator to place the interface in contact with bone of the patient at or proximate the surgical site, and (iv) operating the applicator to apply, to the bone via the interface, energy with parameters of type, intensity, and duration selected for stimulating the healing of bone tissue.

The manipulating of the applicator to place the interface in contact with bone of the patient may be performed prior to the manipulating of the surgical instrument to place the operative or end effector thereof in contact with bone tissue of the patient at the surgical site. The operating of the applicator to apply the energy to the bone preferably takes place at least partially during the using of the surgical instrument to surgically operate on the bone tissue at the surgical site. The operating of the applicator to apply the energy to the bone optionally takes place at least partially prior to and/or after the surgical instrument is used to operate on the bone tissue at the surgical site.

The bone stimulating energy may be ultrasonic mechanical vibrational energy, electrical current, or magnetic field energy. The electrical current arises from the generation of an electrical field.

Preferably, the manipulating of the applicator to place the interface in contact with bone of the patient includes attaching at least a part of the applicator to the bone of the patient. The attaching step may include operating jaws or a clamp, inflating a balloon, or inserting a screw. Typically, the applicator is temporarily attached to the bone and is removed at or prior to the termination of the interventional procedure. However, the applicator may be part of an implant which remains in the patient after the termination of the interventional procedure. In that case, the applicator may be activated postoperatively to continue the application of energy to the bone for stimulating healing, cellular and histological repair and growth processes.

The interface is preferably maintained in contact with the bone of the patient during at least a twenty minute period, the applying of energy to the patient being undertaken during a major portion of the twenty minute period. The application of bone stimulating energy may last essentially the length of entire interventional procedure, for several hours or more. The energy may be applied with modulated intensity and at intervals or in pulses to delimit any undesirable effects on the bone tissue.

As indicated above, the method may incorporate a pretreatment procedure including an applying of pretreatment energy to the patient in a region about the surgical site, the pretreatment energy is taken from the group consisting of ultrasonic mechanical vibrational energy, electrical current, and magnetic field energy. Alternatively or additionally, the method may further comprise subjecting the patient to a post-treatment procedure including an applying of post-treatment energy to the patient in a region about the surgical site, the post-treatment energy is taken from the group consisting of ultrasonic mechanical vibrational energy, electrical current, and magnetic field energy.

A medical kit comprises a surgical instrument having an operative tip or end effector and further comprises an applicator of energy taken from the group consisting of ultrasonic mechanical vibrational energy, electrical current, and magnetic field energy, the applicator being different from the surgical instrument and separate therefrom, the applicator having an energy-transmitting interface, the applicator being configured for attachment directly to a bone of a patient so that the interface is in effective energy-transmitting contact with the bone. The kit may comprise an additional applicator of energy taken from the group consisting of ultrasonic mechanical vibrational energy, electrical current, and magnetic field energy, the additional applicator being different from both the surgical instrument and first applicator and separate therefrom. The kit then includes one or more connector components such as adhesive strips, bands, belts, bandages, and pressurizable fluid-filled bladders for attaching the additional applicator to the patient at an external surface of the patient spaced from the bone and in effective energy-transmitting contact with the external surface.

A medical kit may alternatively comprise a first applicator of energy taken from the group consisting of ultrasonic mechanical vibrational energy, electrical current, and magnetic field energy, the applicator having an energy-transmitting interface, the applicator being configured for attachment directly to a bone of a patient so that the interface is in effective energy-transmitting contact with the bone. One or more first connector components are provided for attaching the first applicator directly to the bone of the patient and in effective energy-transmitting contact with the bone. The comprises a second applicator of energy taken from the group consisting of ultrasonic mechanical vibrational energy, electrical current, and magnetic field energy, the second applicator being different from first applicator and separate therefrom. One or more second connector components are provided for attaching the second applicator to the patient at an external surface of the patient spaced from the bone and in effective energy-transmitting contact with the external surface.

The first connector components may be adhesive layers, screws, clamps, jaws, adhesive strips, bands, belts, bandages, or pressurizable fluid-filled bladders, while the second connector components may be adhesive layers or strips, bands, belts, bandages, or pressurizable fluid-filled bladders.

The kit may additionally comprising a third applicator of energy taken from the group consisting of ultrasonic mechanical vibrational energy, electrical current, and magnetic field energy, the third applicator being different from first applicator and the second applicator and separate therefrom.

DETAILED DESCRIPTION

Figures 1, 2, 3:
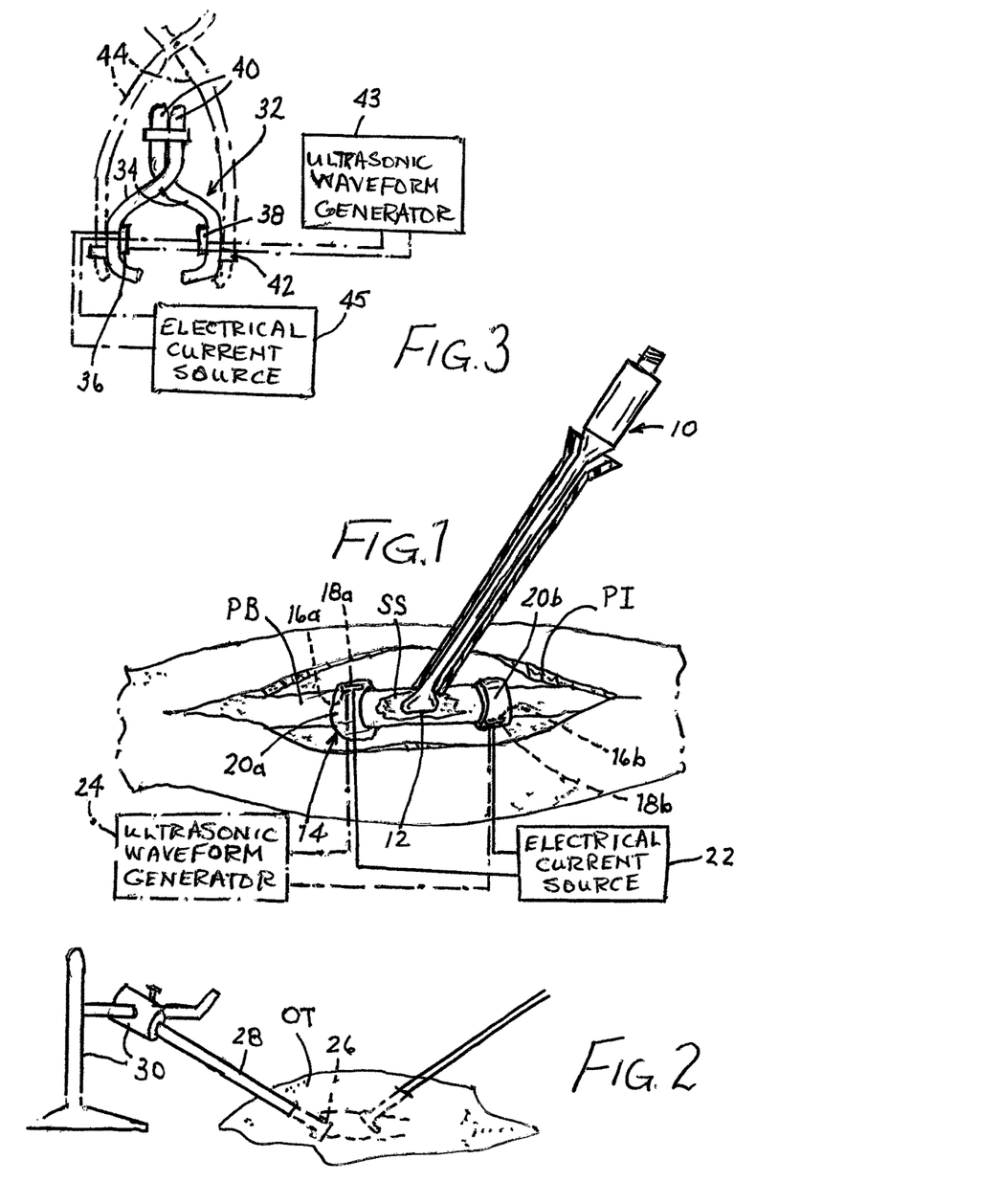
FIG. 1 is a schematic perspective view, partially in cross-section and showing block diagrammatic elements, of a surgical procedure including instruments for the application of energy directly to the bone for stimulating natural bone healing.
FIG. 2 is another perspective view, partially in cross-section, of a surgical procedure including instruments for the application of energy directly to the bone for stimulating natural bone healing.
FIG. 3 is partially a schematic side elevational view and partially a block diagram of a device for applying electrical or ultrasonic waveform energy directly to a bone during an interventional procedure.

As depicted in FIG. 1, a surgical method utilizes a surgical instrument 10 having an operative tip or end effector 12 placed in contact with a preselected surgical site SS on or in a bone PB of a patient's limb PL. The method also utilizes an applicator 14 for conducting energy directly into bone PB at or proximate the surgical site SS to stimulate natural cellular healing processes in the bone tissue at the time of a surgical intervention involving instrument 10. Instrument 10 exemplarily takes the form of an ultrasonic dissector or osteotome but may be any surgical instrument that is used to perform a therapeutic intervention on bone PB.

Applicator 14 is typically placed into effective energy-transmitting contact with bone PB near the beginning of the interventional procedure, for instance, once an incision PI has been made and bone PB exposed. Applicator 14 has at least one energy-transmitting interface or surface 16 that contacts bone PB. Energy-transmitting interface or surface 16 may be active, for instance, a surface of a transducer or electrode or passive, such as an adhesive layer or a casing in an energy transmitting association with an active element.

An interventional procedure includes manipulating instrument 10 to place the operative or end effector 12 in contact with tissue of bone PB at surgical site SS and using instrument 10 to surgically operate on the bone tissue at surgical site SS. The interventional procedure further includes manipulating applicator 14 to place interface 16 in contact with bone PB at or proximate surgical site SS and operating applicator 14 to apply, to bone PB via interface 16, energy with parameters of type, intensity, and duration selected for stimulating the healing of bone tissue.

As discussed in detail hereinafter, the energy applied via applicator 14 may be electrical current (necessarily entailing an electrical field), ultrasonic mechanical vibratory energy, or magnetic field energy. The direct bone stimulation during the interventional procedure causes better healing rates subsequent to the bone intervention procedure.

As depicted in FIG. 1, applicator 14 includes a pair of electrodes 18a and 18b attached to bone PB by means of a pair of adhesive strips, bands, belts, bandages, or pressurizable fluid-filled bladders 20a and 20b. Interface 16 includes a surface 16a of electrode 18a and a surface 16b of electrode 18b. Electrodes 18a and 18b are operatively connected to a source of electric field energy, that is, a current or voltage source 22, for conducting an electrical current, DC or AC, into bone PB on opposite sides of surgical site SS. Thus, the applied energy evinces an electrical current (if only a microcurrent, for instance, where the electrical field strength is small and the rate of oscillation high) applied in a bipolar circuit configuration with the electrodes acting as anode and cathode. One skilled in the art would recognize that the electrical current may be applied in a monopolar circuit configuration, with one electrode 18a or 18b placed on bone PB at or near surgical site SS and the other electrode 18b or 18a exemplarily placed on a skin surface of the patient.

It will be apparent from discussion hereinbelow that electrodes 18a and 18b may take alternative forms for the application of different forms of energy. For instance, electrodes 18a and 18b can be piezoelectric transducers suitable for the generation of sonic or ultrasonic vibrations in the tissues of bone PB at surgical site SS. In that case, the transducers are connected to a source 24 of electrical waveform energy producing an electrical signal having a sonic or ultrasonic frequency. One might use only one transducer if it can be positioned sufficiently close to surgical site SS. In the case of two transducers as shown in FIG. 1, the transducers are activated in synchronization to limit destructive interference of the bone vibrations at the surgical site SS.

Electrodes or transducers 18a and 18b are energized to conduct a predetermined amount of energy into bone PB for a preselected period of time during the interventional procedure, which energy is effective to stimulate healing processes in the bone. Applicator 14 incorporates or is operatively linked to energy source 22 or 24 which is designed to generate electrical energy (DC, AC) of a predetermined intensity for the preselected period of time. The energy may be applied in pulses or at intervals within the prescribed period. For instance, electrical current or mechanical vibrations may be generated in bone PB and conducted into or through the tissues at surgical site SS in pulses having durations of between several microseconds up to several minutes with interpulse intervals likewise ranging from several microseconds to a minute or more.

Typically interfaces 16a and 16b of electrodes or transducers 18a and 18b are placed into contact with bone PB prior to the manipulating of surgical instrument 10 to place the operative or end effector 12 thereof in contact with surgical site SS. Applicator 14 is operated to apply the energy to bone PB at least partially during the using of surgical instrument 10 to surgically operate on tissue at surgical site SS. The operating of applicator 14 to apply energy to bone PB may commence prior to the contact of end effector 12 with surgical site SS and may terminate only after surgical instrument 10 is finally withdrawn from the surgical site.

It is contemplated that applicator 14, and particularly electrodes or transducers 18a and 18b, is only temporarily attached to bone PB and is removed at or prior to the termination of the interventional procedure, that is prior to the closure of incision PI. However, the applicator 14 may be incorporated in part into an implant which remains in the patient after the termination of the interventional procedure. In that case, the applicator may be activated postoperatively to continue the application of energy to the bone for stimulating healing, cellular and histological repair and growth processes.

Applicator interface 16 is preferably maintained in contact with bone PB for at least a twenty minute period, the applying of energy to the patient being undertaken during a major portion of the twenty minute period. The application of bone stimulating energy may last essentially the length of entire interventional procedure, for several hours or more. The energy may be applied with modulated intensity and at intervals or in pulses to delimit any undesirable effects on the bone tissue.

As shown in FIG. 2, an interventional procedure may be a minimally invasive procedure to correct a clinical problem involving a bone structure in the body. In that case, an energy applicator 26 may be disposed at the distal end of a thin rod or shaft 28 (or more than one in the case of bipolar electrical stimulation) that is inserted through the patient's overlying tissues OT, Applicator rod or shaft 28 may be held in place during the interventional procedure by a mounting frame 30 external to the patient.

FIG. 3 illustrates an applicator 32 that delivers bone stimulating energy directly to a bone treatment site intraoperatively. Applicator 32 includes a set of jaws 34 that carry, for instance, anode and cathode electrodes or, alternatively one or more piezoelectric crystal transducers, 36 and 38. Jaws 34 allow for placement of energy transmitting components of applicator 32 on the bone at or proximate a treatment site so that the bone stimulating energy can be applied directly into the bone treatment site. Jaws 34 enable a placement of electrodes or transducers 36 and 38 and a temporary fixation thereof to the target bone via a clamping mechanism so that the applicator 32 remains in place during the entire length of the operation. Jaws 34 may be truncated, with short tails 40 so as to minimize interference with the surgical instrumentation used during the interventional procedure. In that case, jaws 34 may be provided along oppositely facing outer surfaces with eyelets 42 for receiving jaws 44 of an installation tool which is removed after placement and closure of jaws 34. Alternatively, jaws 34 may have extended tails that serve as hand grips for applicator installation and removal. An electrical current source 43 or alternatively an ultrasonic waveform generator 45 is provided for energizing electrodes or transducers 36, 38.

Where electrodes or transducers 36 and 38 deliver AC electrical energy to the surgical site, the electrodes are preferably configured to enable delivery of electric field energy or current to the entire area of intended bone stimulation. Thus, electrodes 36 and 38 are large enough to provide an adequate cross-section of current transmission through the bone. The electric field, stimulating bone natural healing processes, may continue for the entire duration of the operation. It is to be understood that electrical current and electrical field generation in the target bone tissues are naturally coextensive spatially and temporally.

Figure 4:
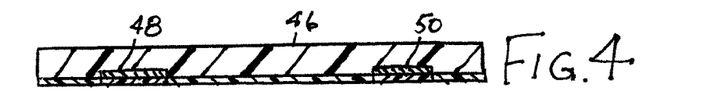
FIG. 4 is a schematic cross-sectional view of an energy applicator including a pad.

FIG. 4 depicts an electrode pad 46 that is placed at a treatment site to deliver electrical energy for bone stimulation. Electrode pad 46 contains both an anode 48 and cathode 50 that delivers DC electrical energy to the treatment site during an operation. Bone stimulation pad 46 can be attached to the bone treatment site by an optional clip to hold the pad in place. Pad 46 delivers AC electric energy, i.e., alternating electric fields. Electrodes 48 and 50 are configured to create electric fields that cover the entire bone treatment site sufficient to deliver bone-stimulating energy simultaneously.

Figure 5:
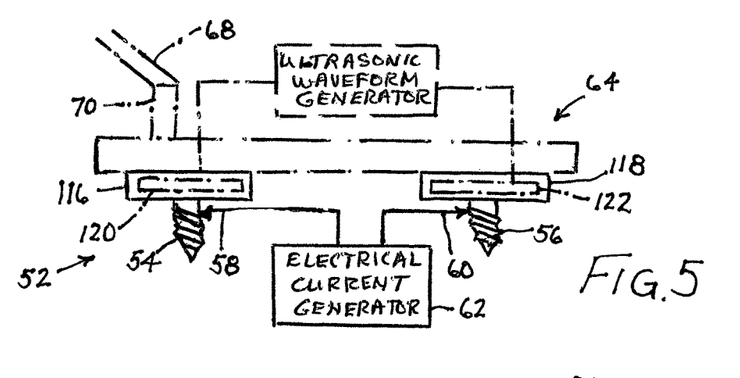
FIG. 5 is partially a schematic side elevational view and partially a block diagram of another device for applying electrical or ultrasonic waveform energy directly to a bone during an interventional procedure.

As illustrated in FIG. 5, an applicator 52 includes one or more screws 54 and 56 implanted into bone at or proximate to a surgical site. Screws 54 and 56 are operatively connected, e.g., via wires 58 and 60, to an electrical current generator 62 deliver electric energy into the bone through the screw. The resulting bone stimulation occurs at the treatment site directly adjacent to the area where bone fusion needs to occur.

Screws 54 and 56 may be removed on termination of the intervention procedure. Pursuant to another option, screws 54 and 56 are parts of a permanent implant 64 that includes a port 70 that serves as bone spacing repair hardware. A probe 68 is connectable to port 70 on the implant 64 to deliver bone stimulating electrical energy through the bone repair implant to the bone treatment site direct adjacent to the implant where fusion needs to occur.

Figure 6:
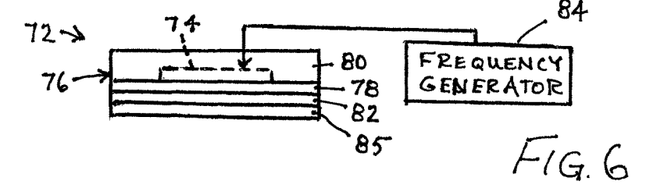
FIG. 6 is partially a schematic side elevational view and partially a block diagram of a further device for applying ultrasonic waveform energy directly to a bone during an interventional procedure.

As shown in FIG. 6, an applicator 72 includes a piezoelectric transducer 74 disposed in a pad 76 including a lower layer 78, an upper layer 80, and an adhesive layer 82. Adhesive layer 82 and lower layer 78 transmit bone stimulating ultrasound energy generated by transducer 74 in response to an electrical waveform produced by a source or generator 84. Typically, a protective cover layer 85 is disposed over adhesive layer 80 and is peeled away prior to the attachment of pad 76 to a bone PB (FIG. 1) in an interventional procedure. Adhesive layer 80 secures pad to or near the treatment area so that transducer 74 is held in place for the duration of the intervention. The securing means can alternatively include a clip or a set of locking jaws, that allows the probe to remain in constant contact with the treatment area while bone stimulating ultrasound energy is being applied.

Figure 7:
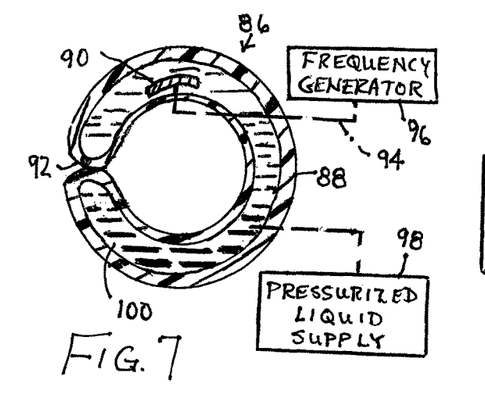
FIG. 7 partially a schematic cross-sectional view and partially a block diagram of yet another device for applying ultrasonic waveform energy directly to a bone during an interventional procedure.

FIG. 7 depicts an applicator 86 including a slotted flexible carrier balloon or bladder 88 which contains a piezoelectric ultrasound transducer 90. Balloon or bladder 88 has an inflated form that is annular with a slot or gap 92 for enabling a user to slip the balloon or bladder in a deflated state about a bone that has been accessed for treatment in an interventional procedure. Transducer 90 is operatively connected via lead or wire 94 to a waveform generator or source 96 and in response to a signal therefrom produces bone stimulating ultrasound energy which is conducted into bone tissue at the interventional treatment site. Balloon or bladder 88 is coupled with a source 98 of pressurized liquid 100 such as saline solution which is fed to the balloon or bladder for inflating the same the enable an effective pressure-wave-transmitting contact with bone at a surgical treatment site. The saline solution is a conductive medium that transmits the ultrasound energy from the transducer 90 to the bone at or proximate the interventional treatment site. The flexible applicator 86 allows for placement and positioning so that it can be left in place for the duration of the interventional procedure.

Figure 8:
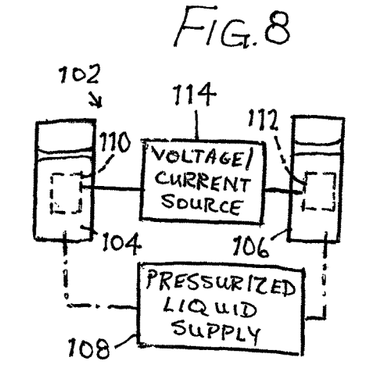
FIG. 8 is partially a schematic side elevational view and partially a block diagram of yet a further device for applying electrical current directly to a bone during an interventional procedure.

FIG. 8 shows an applicator 102 including a pair of slotted annular bladders 104 and 106 which are connected to a source 108 of pressurized fluid. Bladders 104 and 106 carry, on inner surfaces of the toroidal forms, respective electrodes 110 and 112 that are pressed by the inflated bladders against a bone PB (FIG. 1) on opposite sides of surgical site SS for conducting electrical current through the bone tissue at the surgical site. The electrical current arises from an electrical field generated in the bone tissue by an electrical current or voltage source 114 and electrodes 110 and 112. It is possible to dispose electrodes 110 and 112 on a single bladder configured to position the electrodes on opposite sides of a target treatment area on a bone. Such a bladder may be formed, for instance, with a window for accessing the treatment area. The bladder may be provided with reinforcement for reducing inadvertent damage to the bladder by surgical instruments.

As depicted in FIG. 5, applicator 52 may alternatively serve for the conduction of ultrasonic (or sonic) vibratory energy into a target bone PB (FIG. 1). In that case, at least one body or frame 116, 118 contains a piezoelectric transducer element 120, 122 that is fixed to a respective screw 54, 56 for generating therein an ultrasonic vibration (preferably a standing wave of an ultrasonic frequency) that is conducted into the bone tissue at or near an interventional site SS (FIG. 1). Alternatively, a separate ultrasound probe may be used as a driver to place implant hardware like screws 54, 56 into bone. The driver head has an ultrasound conducting material such that it transmits the bone stimulating ultrasound energy into the bone through the screw. The resulting bone stimulation occurs at the treatment site directly adjacent to the area where bone fusion needs to occur.

Figure 9:
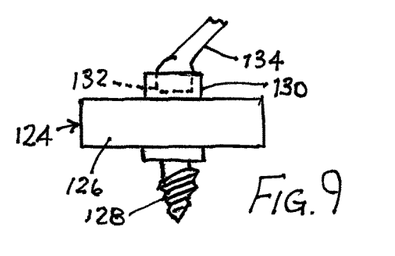
FIG. 9 is a schematic side elevational view of an applicator device for applying vibratory waveform energy directly to a bone during an interventional procedure.

FIG. 9 schematically shows an implant 124 that serves as bone spacing or bone repair hardware including a body or frame member 126 and at least one screw 128. Body or frame member 126 is provided with a port element 130 that receives a distal end 132 of an ultrasound probe 134. The probe 134 delivers bone stimulating ultrasound energy through the bone repair implant 124 directly to the bone treatment site, adjacent to the implant, where fusion needs to occur.

The method may incorporate a pretreatment procedure including the application of pretreatment energy to the patient in a region about the surgical site. The pretreatment energy may be ultrasonic mechanical vibrational energy, electrical current, or magnetic field energy. Alternatively or additionally, the method may further comprise subjecting the patient to a post-treatment procedure including an applying of post-treatment energy to the patient in a region about the surgical site. The post-treatment energy is ultrasonic mechanical vibrational energy, electrical current, or magnetic field energy.

Figure 10:
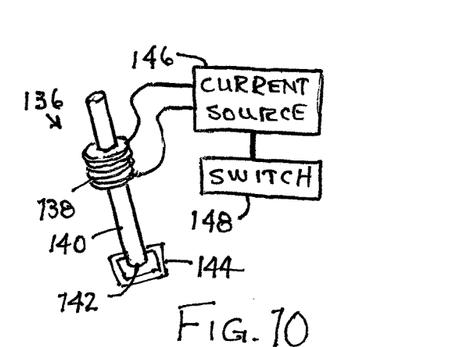
FIG. 10 is partially a schematic perspective view and partially a block diagram of a device for applying magnetic field energy directly to a bone during an interventional procedure.

The stimulation of natural bone repair processes can be achieved by the application of magnetic field energy. FIG. 10 illustrated an electromagnet 136 with wire windings 138 wrapped around an extended core 140. A distal end 142 of core 140 may be placed into contact with and held against the bone PB (FIG. 1) during an interventional procedure as discussed hereinabove. Electromagnet 136 and particularly core 140 may be provided with a fixation member 144 such as a clamp, band, bracket and set screw, etc. for attaching the electromagnet to the bone during the interventional procedure. Windings 138 are connected to a current source 146 that is configured for the generation of a gentle magnetic field. In the event that metal instrument are used to conduct the surgical operation, current source 146 may be provided with a switch 148 for turning the magnet off when a metal instrument is moved near core 140.

Figure 11:
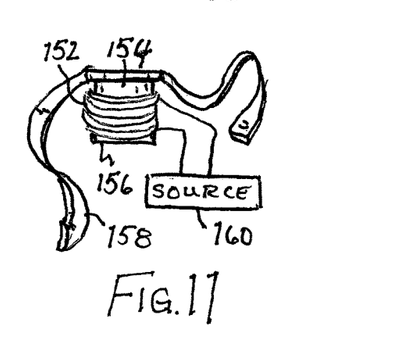
FIG. 11 is partially a schematic perspective view and partially a block diagram of a device for applying magnetic field energy directly to a bone during an interventional procedure, post operatively or during a pretreatment procedure.

Because of the potential interference with the manipulation of the surgical instrumentation, magnetic fields are better used for preoperative and postoperative treatment. FIG. 11 depicts an electromagnet 150 with wire windings 152 wrapped around a short core 154. One side 156 of core 154 may be placed into contact with and held against a skin surface of a patient during an interval prior to or after an interventional procedure. Electromagnet 150 is provided with a fixation member 158 such as a clamp, band, bracket and set screw, etc. for attaching the electromagnet to the bone during the interventional procedure. Windings 138 are connected to a current source 160 that is configured for the generation of a gentle magnetic field.

Ultrasound applied in an intraoperative bone healing process is generated in low frequency ranges, below 100 Khz. While a wide variety of energy densities can be used, energy densities in the 25 mW/cm$^2$-45 mW/cm$^2$ range are preferred. These energy densities appear to deliver the most optimal energy density while maintaining no or limited thermal response in the bone.

Since application of healing-stimulating energy pursuant to the present invention is directly to bone tissue, transmission through soft tissues overlying the treatment site is avoided, so that higher energy densities can be delivered while staying below thermal damage thresholds and upper limits. Thus a wide range of bone stimulation parameters can be used for direct interventional ultrasound application for advancing natural cellular healing and tissue repair processes.

Where ultrasound is applied in a pretreatment phase prior to interventional surgery or in a post treatment phase after the surgery has been completed, the ultrasound waves may be generated in the tissues of the patient via a plurality of transducers in contact with the patient at a plurality of spaced locations, for instance, around a limb. The operation of the mutually spaced transducers is synchronized so that the ultrasound waves interfere in the surgical treatment area below the skin surface. Thus the energies applied to the skin and other tissues overlying the surgical treatment site are minimized relative to the total energy generated in the bone tissues at the surgical treatment site. The ultrasound transducers may be operated as phased arrays or may be shaped for soft focusing of ultrasound waveform energy at the surgical site.

The duration of energy application may include a wide variety of protocols. For example, interventional direct application of bone stimulating ultrasound can be applied for the length of a surgical procedure and initiated once the surgeon has gained access to the treatment area. A preferred approach is direct application of bone stimulating energy for a minimum of 20 minutes during the surgical intervention and a maximum of the entire length of the surgical procedure, which may last several hours.

The application of the therapeutic energy may be continuous or intermittent. For instance, the energy may be applied in pulses each ranging in duration from a few microseconds to several minutes. The interpulse durations may likewise vary in duration from a few microseconds to several minutes.

Figure 12:
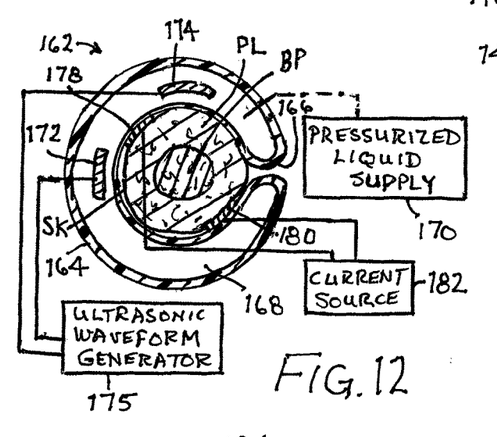
FIG. 12 is partially a schematic cross-sectional view and partially a block diagram of a device for applying electrical current and/or mechanical vibratory energy to a patient either before or after interventional surgery.

FIG. 12 illustrates an applicator 162 for use in a pretreatment or post operative treatment procedure. Applicator 162 includes an attachment member 164 in the form of an annular bladder optionally formed with a slot 166 for facilitating a slipping of the bladder over a limb PL of a patient prior to or after an interventional procedure treating a bone BP. Bladder 164 has an internal chamber 168 that can be expanded with liquid under pressure from a source or supply 170. Chamber 168 contains one or more sonic or ultrasonic transducers 172, 174 each in the form of a single piezoelectric crystal or an array (e.g., phased array) of piezoelectric transducer elements. Transducers or arrays 172, 174 are operatively connected to a source 175 of electrical signals such as alternating waveforms.

As further illustrated in FIG. 12, an inner surface 176 of bladder 164 carries a pair of electrodes 178 and 180 engageable with a skin surface SK of the patient over bone BP. Electrodes 178 and 180 are connected to a source 182 of DC or AC current.

Figure 13:
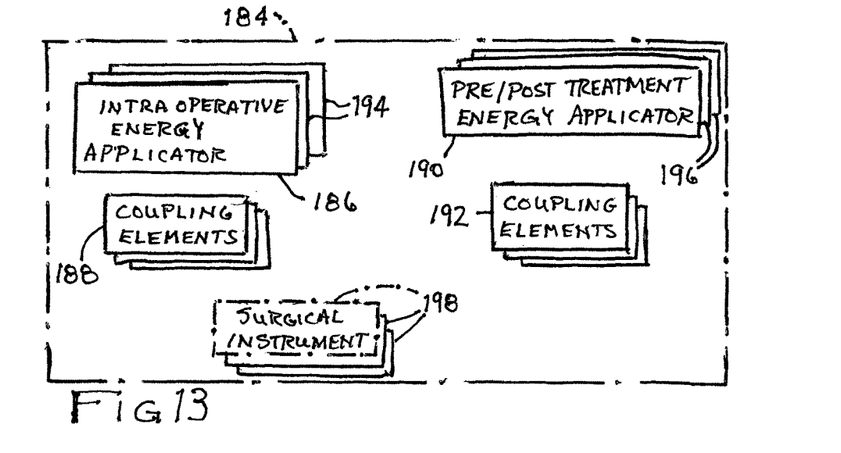
FIG. 13 is a block diagram of a kit containing various applicators of energy for enhancing or stimulating natural bone healing processes, useful in conjunction with an interventional surgical procedure.

FIG. 13 diagrammatically depicts a kit 184 for use in interventional bone surgery. Kit 184 includes an applicator 186 of intraoperative bone healing energy that includes a coupling element 188 for attaching the applicator directly to a bone surface for generating therapeutic/healing energy in bone tissues at a surgical site. Coupling element 188 may take any suitable form, including but not limited to screws, clamps, jaws, adhesive strips, adhesive layers, bands, belts, bandages, or pressurizable fluid-filled bladders. Kit 184 further includes a second applicator 190 for use in applying bone healing energy to a surgical site in a pretreatment and/or post treatment therapy regimen. Applicator 190 is designed for placement on an external skin surface, spaced from the bone which is subjected to surgical encroachment during an interventional procedure. Applicator 190 includes a coupling element 192 for attaching the applicator on an external surface of the patient. Coupling element 192 may take any suitable form, including but not limited to clamps, jaws, adhesive strips, adhesive layers, bands, belts, bandages, or pressurizable fluid-filled bladders. Kit 184 may include one or more additional applicators 194 of intraoperative bone healing energy. The energy produced by applicators 194 may be of a type that is the same as or different from the energy produced by applicator 186. Thus, kit 184 optionally includes one or more applicators of mechanical vibratory energy, one or more applicators of electrical current, and/or one or more applicators of magnetic field energy. Likewise, kit 184 may include one or more additional applicators 196 of pretreatment and/or post treatment energy, where the type of energy applied may vary from one applicator to the next. Each applicator may have its own coupling element (not shown). Suitable energy sources or generators (not shown in FIG. 13) can be provided with kit 184 or sold separately. The energy sources or generators may be used to drive both extended treatment (pre- and post-operative) and intraoperative applicators, where the types of treatment involve the same type of energy.

Kit 184 may also include one or more instruments or probes 198 for performing the intraoperative surgery.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
providing a surgical instrument having an operative tip or end effector configured for ablating or dissecting bone tissue;
providing an applicator of energy, said applicator being different from said surgical instrument and separate therefrom, said applicator having an energy-transmitting interface; and
conducting an interventional procedure including:
manipulating said instrument to place said operative or end effector in contact with a bone of a patient at a surgical site;
using said surgical instrument to surgically ablate or dissect the bone tissue at said surgical site;
prior to a termination of said interventional procedure, manipulating said applicator to place said interface in contact with the bone of the patient at or proximate said surgical site; and
operating said applicator to apply, to the bone via said interface, energy with parameters of type, intensity, and duration selected for stimulating the healing of the bone,
wherein the manipulating of said applicator to place said interface in contact with the bone of the patient is performed prior to the manipulating of said instrument to place said operative or end effector in contact with the bone at the surgical site.

2. The method defined in claim 1 wherein the operating of said applicator to apply said energy to the bone takes place at least partially during the using of said surgical instrument to surgically ablate or dissect the bone at said surgical site.

3. The method defined in claim 2 wherein said energy is taken from the group consisting of mechanical vibrational energy, electrical current, and magnetic field energy.

4. The method defined in claim 2 wherein the manipulating of said applicator to place said interface in contact with the bone of the patient includes attaching at least a part of said applicator to the bone of the patient.

5. The method defined in claim 1 wherein said energy is taken from the group consisting of mechanical vibrational energy, electrical current, and magnetic field energy.

6. The method defined in claim 1 wherein the manipulating of said applicator to place said interface in contact with the bone of the patient includes attaching at least a part of said applicator to the bone of the patient.

7. The method defined in claim 1, further comprising maintaining said interface in contact with the bone of the patient during at least a twenty minute period, the applying of energy to the patient being undertaken during at least a portion of said at least a twenty minute period.

8. The method defined in claim 1, further comprising maintaining said interface in contact with the bone of the patient during at least a portion of said surgical procedure, the applying of energy to the patient being undertaken during said surgical procedure.

9. The method defined in claim 1, further comprising subjecting the patient to a pretreatment procedure including an applying of pretreatment energy to the patient in a region about said surgical site, said pretreatment energy is taken from the group consisting of mechanical vibrational energy, electrical current, and magnetic field energy.

10. The method defined in claim 1, further comprising subjecting the patient to a post-treatment procedure including an applying of post-treatment energy to the patient in a region about said surgical site, said post-treatment energy is taken from the group consisting of mechanical vibrational energy, electrical current, and magnetic field energy.

11. A surgical method comprising:
providing a surgical instrument having an operative tip or end effector configured for ablating or dissecting bone tissue;
providing an applicator of energy, said applicator being different from said surgical instrument and separate therefrom, said applicator having an energy-transmitting interface; and
conducting an interventional procedure including:
manipulating said instrument to place said operative or end effector in contact with a bone of a patient at a surgical site;
using said surgical instrument to surgically ablate or dissect the bone at said surgical site;
prior to a termination of said interventional procedure, manipulating said applicator to place said interface in contact with the bone of the patient at or proximate said surgical site; and
operating said applicator to apply, to the bone via said interface, energy with parameters of type, intensity, and duration selected for stimulating the healing of the bone,
wherein the operating of said applicator to apply said energy to the bone takes place at least partially during the using of said surgical instrument to surgically ablate or dissect the bone at said surgical site.

12. The method defined in claim 11, further comprising maintaining said interface in contact with the bone of the patient during at least a twenty minute period, the applying of energy to the patient being undertaken during at least a portion of said at least a twenty minute period.

* * * * *